US008764719B2

(12) United States Patent
Bissah et al.

(10) Patent No.: US 8,764,719 B2
(45) Date of Patent: Jul. 1, 2014

(54) ABSORBENT ARTICLE INCLUDING AN ABSORBENT CORE LAYER HAVING A MATERIAL FREE ZONE AND A TRANSFER LAYER ARRANGED BELOW THE ABSORBENT CORE LAYER

(75) Inventors: Kofi Bissah, Somerset, NJ (US); Paul Davies, Hillsborough, NJ (US); Francisco J. V. Hernandez, São Paulo (BR); Fernanda Wiermann Paques, São Paulo (BR)

(73) Assignee: Johnson & Johnson Ind. E Com. Ltda (BR)

( * ) Notice: Subject to any disclaimer, the term of this patent is extended or adjusted under 35 U.S.C. 154(b) by 49 days.

(21) Appl. No.: 12/554,047

(22) Filed: Sep. 4, 2009

(65) Prior Publication Data

US 2011/0060303 A1 Mar. 10, 2011

(51) Int. Cl.
| | | |
|---|---|---|
| A61F 13/475 | (2006.01) | |
| A61F 13/532 | (2006.01) | |
| A61F 13/537 | (2006.01) | |
| A61F 13/53 | (2006.01) | |
| A61F 13/513 | (2006.01) | |
| A61F 13/514 | (2006.01) | |
| A61F 13/539 | (2006.01) | |
| A61F 13/533 | (2006.01) | |
| A61F 13/536 | (2006.01) | |

(52) U.S. Cl.
CPC ........... *A61F 13/53* (2013.01); *A61F 13/53717* (2013.01); *A61F 13/5323* (2013.01); *A61F 13/513* (2013.01); *A61F 13/514* (2013.01); *A61F 13/539* (2013.01); *A61F 13/53756* (2013.01); *A61F 13/4758* (2013.01); *A61F 2013/530875* (2013.01); *A61F 13/533* (2013.01); *A61F 13/536* (2013.01); *A61F 13/4756* (2013.01)
USPC ............................... 604/385.101; 604/385.01

(58) Field of Classification Search
USPC ............. 604/289, 358, 367–369, 374, 385.01
See application file for complete search history.

(56) References Cited

U.S. PATENT DOCUMENTS

| | | | | |
|---|---|---|---|---|
| 4,624,666 | A | * | 11/1986 | DeRossett et al. ............ 604/366 |
| 4,840,692 | A | * | 6/1989 | Kamstrup-Larsen ......... 156/252 |
| 4,973,325 | A | | 11/1990 | Sherrod et al. |
| 4,988,344 | A | | 1/1991 | Reising et al. |
| 5,176,672 | A | * | 1/1993 | Bruemmer et al. ...... 604/385.19 |
| 5,304,161 | A | * | 4/1994 | Noel et al. .................... 604/378 |
| 5,505,720 | A | | 4/1996 | Walters et al. |
| 5,624,423 | A | | 4/1997 | Anjur et al. |
| 5,662,633 | A | | 9/1997 | Doak et al. |
| 5,810,798 | A | * | 9/1998 | Finch et al. ................... 604/378 |
| 5,954,705 | A | | 9/1999 | Sawaki et al. |
| 6,245,962 | B1 | * | 6/2001 | Muhs et al. .................... 604/374 |

(Continued)

FOREIGN PATENT DOCUMENTS

| | | |
|---|---|---|
| EP | 2055279 | 5/2009 |
| WO | WO 86/01378 | 3/1986 |

(Continued)

*Primary Examiner* — Susan Su

(57) ABSTRACT

The present invention generally relates to absorbent articles and in particular to an absorbent article including a liquid permeable cover layer, a liquid impermeable barrier layer, an absorbent core arranged adjacent to the cover layer, a transfer layer arranged between the core and the barrier layer, the absorbent core including an upper surface and a lower surface and a material-free zone extending from the upper surface to the lower surface.

1 Claim, 8 Drawing Sheets

(56) References Cited

U.S. PATENT DOCUMENTS

| | | | |
|---|---|---|---|
| 6,984,225 B2 * | 1/2006 | Raidel et al. | 604/385.101 |
| 7,122,023 B1 * | 10/2006 | Hinoki | 604/385.101 |
| 2003/0045851 A1 | 3/2003 | Vartiainen | |
| 2004/0176734 A1 * | 9/2004 | Rasmussen et al. | 604/380 |
| 2004/0243078 A1 * | 12/2004 | Guidotti et al. | 604/367 |
| 2004/0254554 A1 * | 12/2004 | Mavinkurve et al. | 604/380 |
| 2005/0124953 A1 * | 6/2005 | Woltman et al. | 604/385.01 |
| 2006/0069366 A1 * | 3/2006 | Cole | 604/378 |
| 2009/0112173 A1 | 4/2009 | Bissah et al. | |
| 2010/0256586 A1 * | 10/2010 | Bergstrom et al. | 604/385.24 |
| 2011/0060303 A1 | 3/2011 | Bissah et al. | |

FOREIGN PATENT DOCUMENTS

| WO | WO 91/09582 | 7/1991 |
| WO | WO 95/17869 | 7/1995 |
| WO | WO 01/97736 | 12/2001 |
| WO | WO 2009067059 A1 * | 5/2009 |

\* cited by examiner

ABSORBENT ARTICLE INCLUDING AN ABSORBENT CORE LAYER HAVING A MATERIAL FREE ZONE AND A TRANSFER LAYER ARRANGED BELOW THE ABSORBENT CORE LAYER

FIELD OF INVENTION

The present invention generally relates to absorbent sanitary napkins and in particular to a sanitary napkin that has superior transverse and longitudinal wicking characteristics, as well as superior fluid penetration time and rewet properties.

BACKGROUND OF THE INVENTION

In order for a sanitary napkin to efficiently absorb a large amount of fluid during use it must effectively wick fluid throughout the absorbent structure of the napkin. Absent effective wicking properties menstrual fluid tends to pool in certain regions of the napkin as a result of which the full absorbent capacity of the napkin is not effectively utilized. Accordingly, the inventors of the present invention have recognized a need to provide a sanitary napkin that efficiently wicks fluid in the longitudinal and transverse directions of the napkin to thereby fully utilize the full absorbent capacity of the napkin, while also providing superior fluid penetration time and rewet properties.

SUMMARY OF THE INVENTION

In view of the foregoing, the present invention provides, according to first aspect of the invention, an absorbent article including a longitudinally extending centerline, a transversely extending centerline, a liquid permeable cover layer having a body facing surface, a liquid impermeable barrier layer, an absorbent core arranged adjacent to the cover layer, a transfer layer arranged between the absorbent core and the barrier layer, the absorbent core including an upper surface and a lower surface and a material-free zone extending from the upper surface to the lower surface, and the cover layer including a first region arranged in spaced relationship to the transfer layer and a second region arranged in surface to surface contact with the transfer layer.

The present invention provides, according to second aspect of the invention, an absorbent article including a longitudinally extending centerline, a transversely extending centerline, a liquid permeable cover layer having a body facing surface, a liquid impermeable barrier layer, an absorbent core arranged adjacent to the cover layer, a transfer layer arranged between the absorbent core and the barrier layer, the absorbent core including an upper surface and a lower surface, the absorbent core including a plurality of beams and a plurality of material-free zones, each of the beams arranged in a spaced relationship to an adjacent beam and each of the beams being separated from an adjacent beam by a material-free zone, each of the material-free zones extending from the upper surface to the lower surface, the cover layer including a plurality of first regions arranged in spaced relationship to the transfer layer and a plurality of second regions, each of the second regions located between two adjacent beams and arranged in surface to surface contact with the transfer layer.

BRIEF DESCRIPTION OF THE DRAWINGS

Examples of embodiments of the present invention will now be described with reference to the drawings, in which.

DETAILED DESCRIPTION OF THE INVENTION

Figure 1:
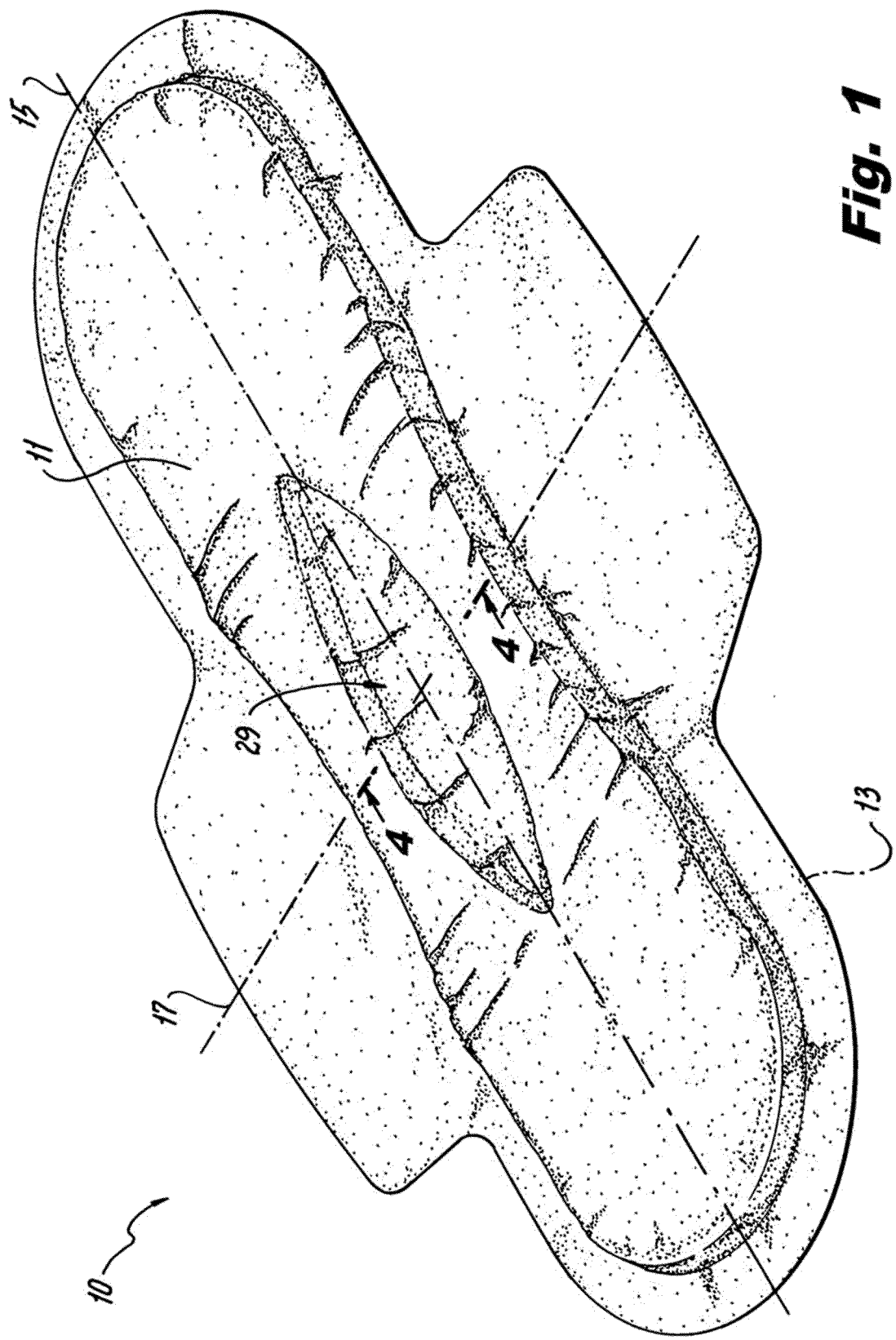
FIG. 1 is a top perspective view of an absorbent article according to the present invention.

The present invention generally relates to disposable absorbent articles such as sanitary napkins, pantiliners, absorbent products for incontinence, and other disposable absorbent articles worn close to a wearer's body. Although the invention will be described herein with reference to a sanitary napkin, the invention may be utilized with other disposable sanitary absorbent articles such as absorbent products for incontinence, diapers, pantiliners and the like.

Absorbent articles according to the present invention provide superior fluid handling characteristics, and more specifically provide superior longitudinal and transverse wicking characteristics, as well as superior fluid penetration time and rewet properties.

As shown in FIGS. 1-4, the present invention relates to a sanitary napkin 10 for absorbing bodily fluids. The sanitary napkin 10 includes a body facing surface 11, a garment facing surface 13, a longitudinally extending centerline 15, and a transversely extending centerline 17.

Figure 3:
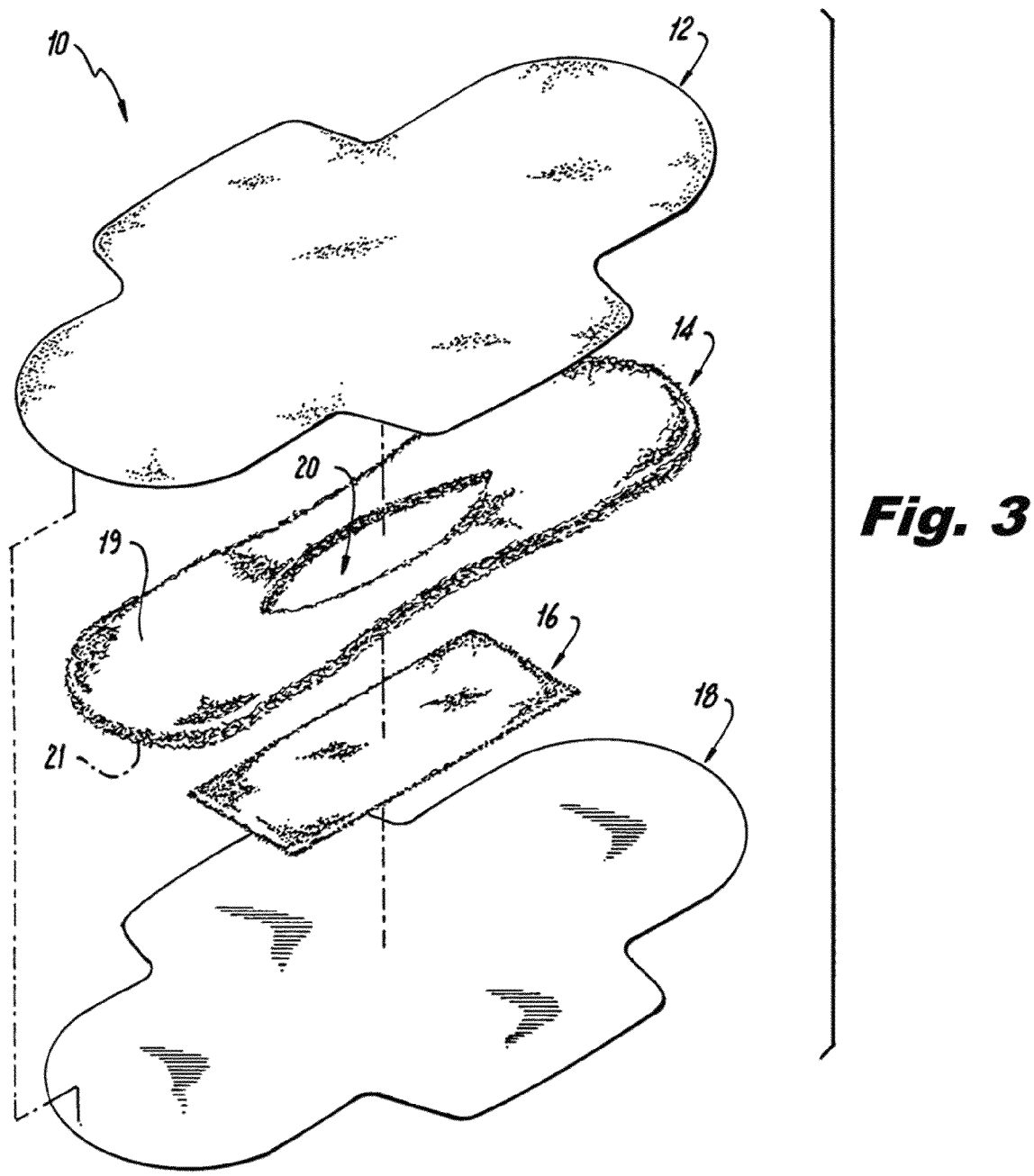
FIG. 3 is an exploded view of the absorbent article shown in FIG. 1 according to a first embodiment of the invention.

As best seen in the exploded view shown in FIG. 3, the sanitary napkin 10 includes a fluid permeable cover layer 12, an absorbent core 14, a transfer layer 16, and a fluid impermeable barrier layer 18. As shown in FIG. 3, the absorbent core 14 is arranged adjacent to the cover layer 12 and the transfer layer 16 is arranged between the absorbent core 14 and the barrier layer 18.

The absorbent core 14 includes a material-free zone 20 that is devoid of any absorbent material. The material-free zone 20 extends from an upper surface 19 of the absorbent core 14 to a lower surface 21 of the absorbent core 14. The material-free zone 20 may be formed by any known method such as cutting or the like. In the specific embodiment of the invention shown in FIGS. 1-4 the material-free zone 20 is centrally aligned with respect to the longitudinally extending centerline 15 and the transversely extending centerline 17. In the specific embodiment of the invention shown in FIGS. 1-4, the material-free zone 20 is substantially elliptical in shape and preferably has a length as measured along the longitudinally extending centerline 15 in the range of about 40 mm to about 160 mm and a width as measured along the transversely extending centerline 17 of about 10 mm to about 60 mm. The material-free zone 20 preferably extends over a surface area in the range of between 400 mm$^2$ and about 6000 mm$^2$.

Figure 4:
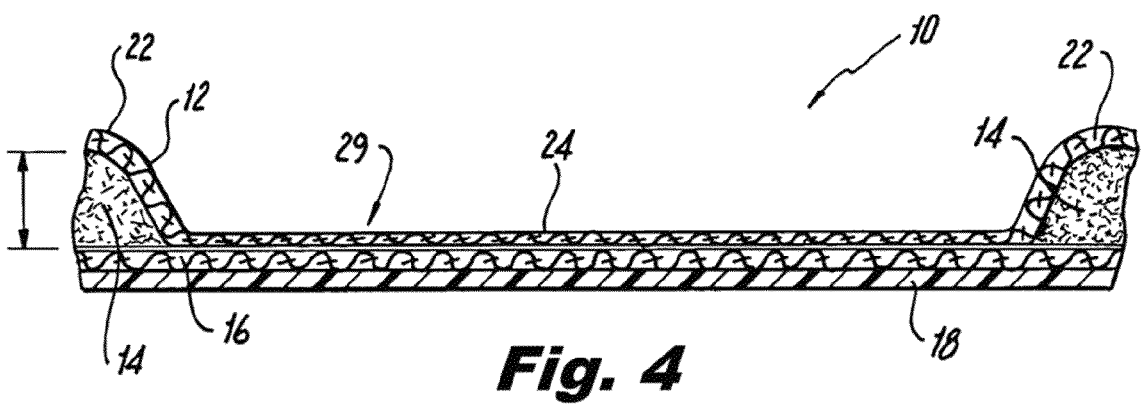
FIG. 4 is sectional view of the absorbent article shown in FIG. 1 taken along line 4-4 in FIG. 1.

As best seen in FIG. 4, the cover layer 12 includes a first region 22 located outside the area of the material-free zone 20 that is arranged in spaced relationship to the transfer layer 16 and the cover layer includes a second region 24 within the area defined by the material-free zone 20 that is arranged in surface to surface contact with the transfer layer 16. The surface to surface contact of the cover layer 12 with the transfer layer 16 essentially defines a gutter 29 in the body facing surface 11 of the napkin 10. The absorbent core 14 preferably has a thickness of between about 0.5 mm and about 20 mm. The depth of the gutter 29 is in the range of between about 0.5 mm and about 20 mm. The thickness and depth measurements set forth in this paragraph may be determined by using a suitable thickness gauge such as the Mitutoyo Absolute Gauge or equivalent.

Figure 5:
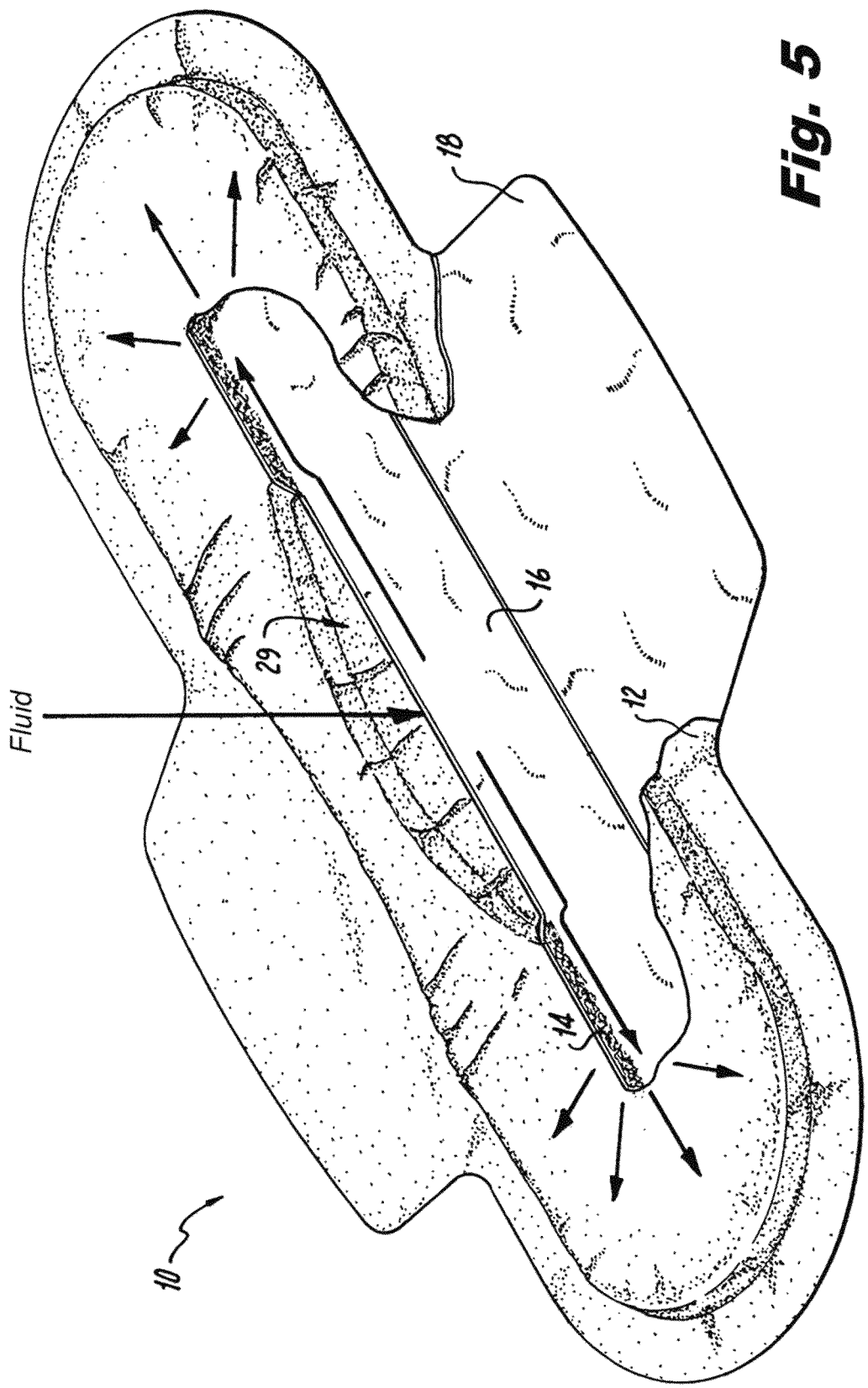
FIG. 5 is partially cut-away perspective view of the absorbent article shown in FIG. 1 schematically depicting the path of fluid flow within the article.

Reference is made to FIG. 5 which depicts the manner in which fluid is conveyed within the absorbent structure of a napkin 10 according to the present invention. As show, the transfer layer 16 directly receives fluid from the cover layer 12 in the area of the material-free zone 20. The transfer layer 16 then wicks the fluid in the longitudinal and transverse directions of the napkin until the fluid can be conveyed upward and absorbed into the absorbent core 14.

Figure 6:
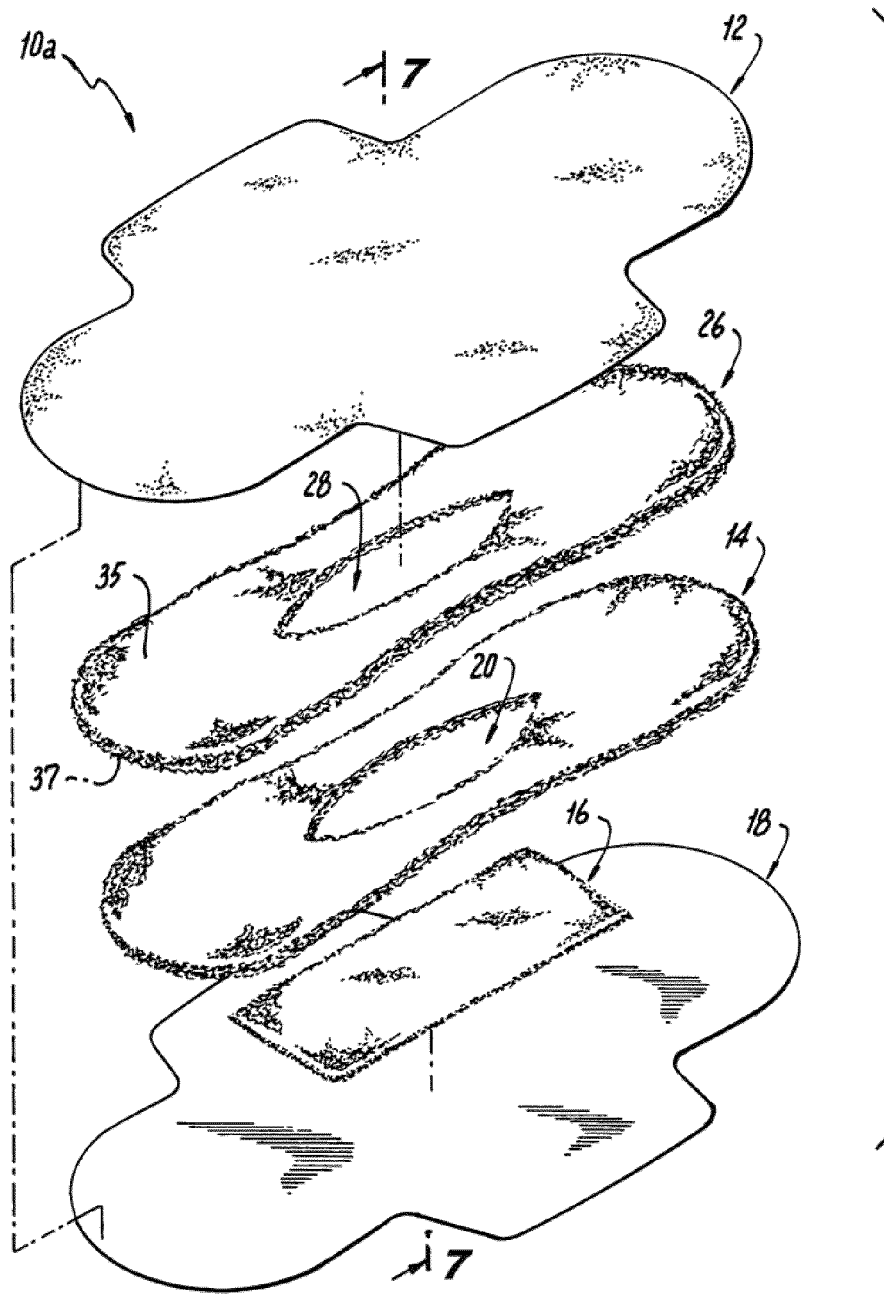
FIG. 6 is an exploded view of the absorbent article shown in FIG. 1 according to a second embodiment of the invention.

Reference is made to FIG. 6 which depicts an exploded view of a sanitary napkin 10a according to a second embodiment of the present invention. The sanitary napkin 10a is similar in structure to the sanitary napkin 10 described above but further includes a secondary absorbent core 26 arranged between the primary absorbent core 14 and the transfer layer 16. As shown, the secondary absorbent core 26 includes a material-free zone 28 that corresponds in size and shape to the material-free zone 20 of the primary absorbent core 14. The material-free zone 28 extends from an upper surface 35 of the secondary absorbent core 26 to a lower surface 37 of the secondary absorbent core 26.

Figure 7:
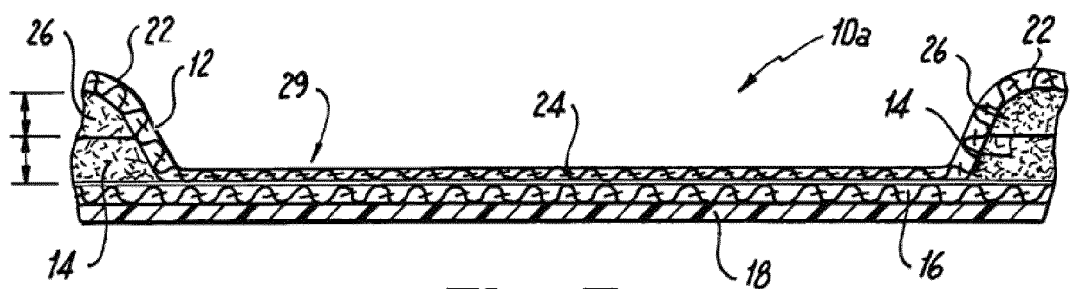
FIG. 7 is a sectional view of the absorbent article shown in FIG. 6 taken along line 7-7 in FIG. 6.

Referring to FIG. 7, the cover layer 12 includes a first region 22 located outside the area of the material-free zones 20 and 28 that is arranged in spaced relationship to the transfer layer 16 and the cover layer includes a second region 24 within area of the material-free zones 20 and 28 that is arranged in surface to surface contact with the transfer layer 16. The surface to surface contact of the cover layer 12 with the transfer layer 16 essentially defines a gutter 29 in the body facing surface of the napkin 10. The primary absorbent core 14 and the secondary absorbent core 28 preferably each has a thickness of between about 0.5 mm and about 20 mm. The depth of each gutter 29 is in the range of between about 1.0 mm and about 40 mm.

Figure 8:
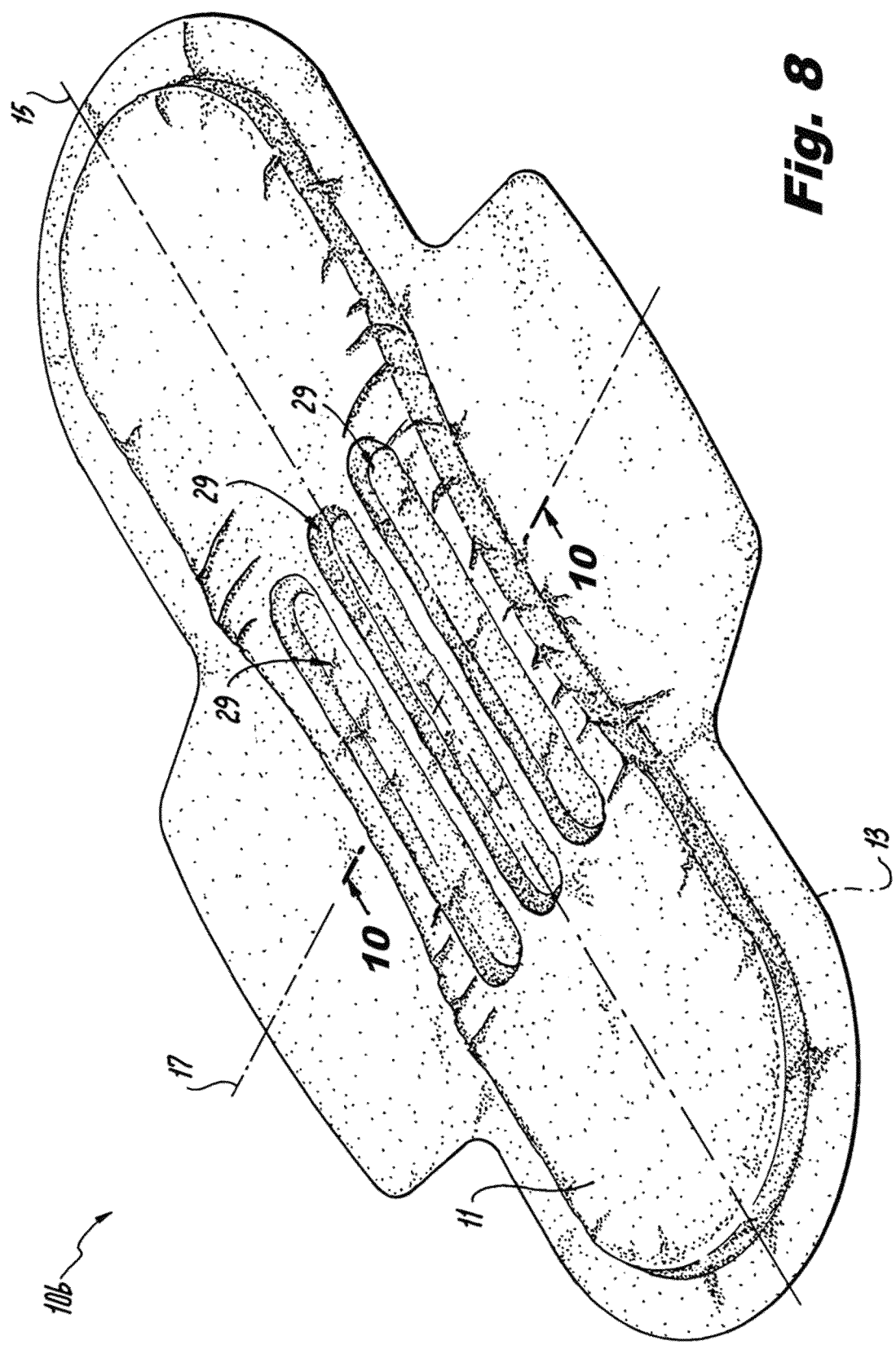
FIG. 8 is a top perspective view of an absorbent article according to a third embodiment of the present invention.
Figure 9:
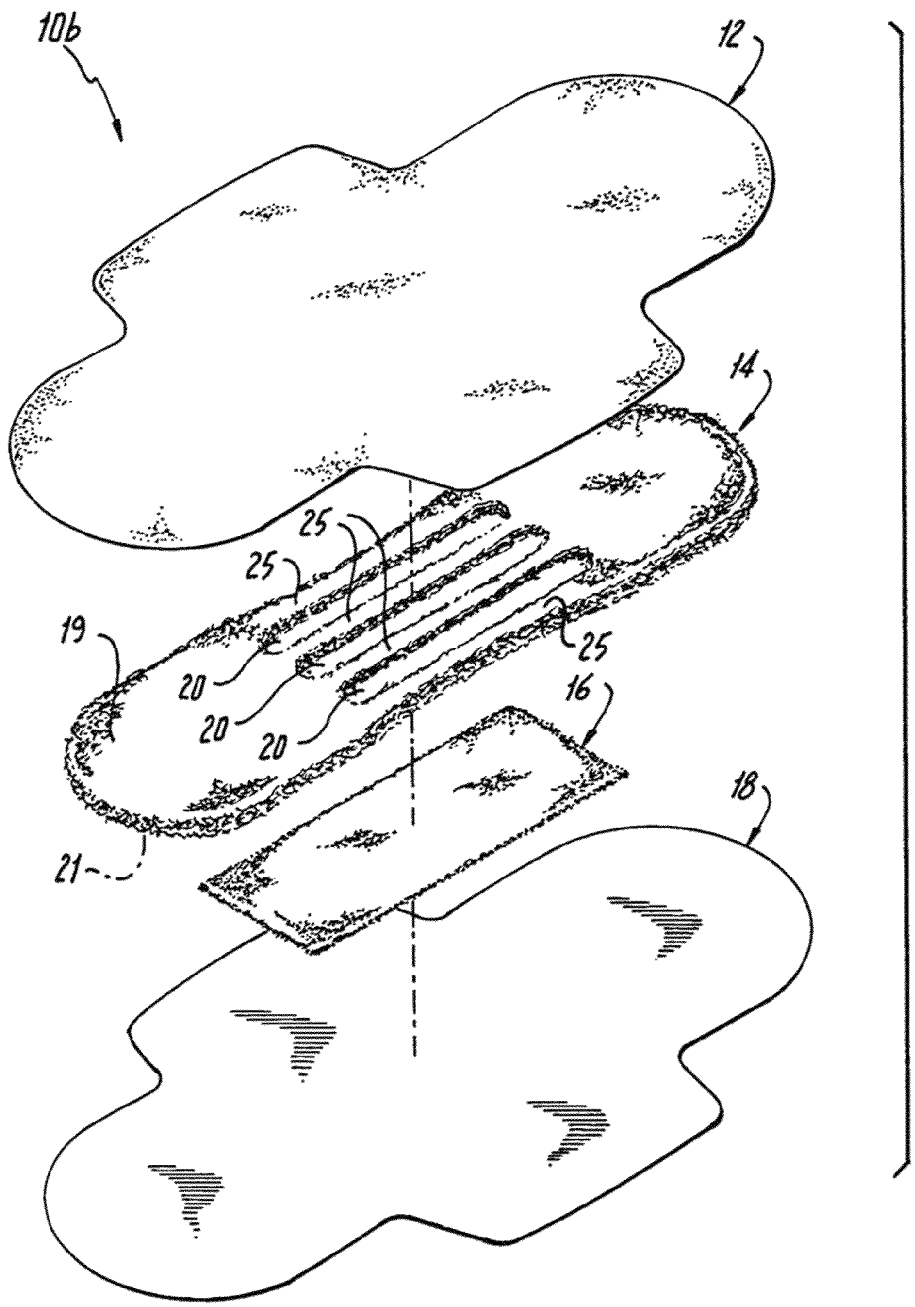
FIG. 9 is an exploded view of the absorbent article shown in FIG. 8.
Figure 10:
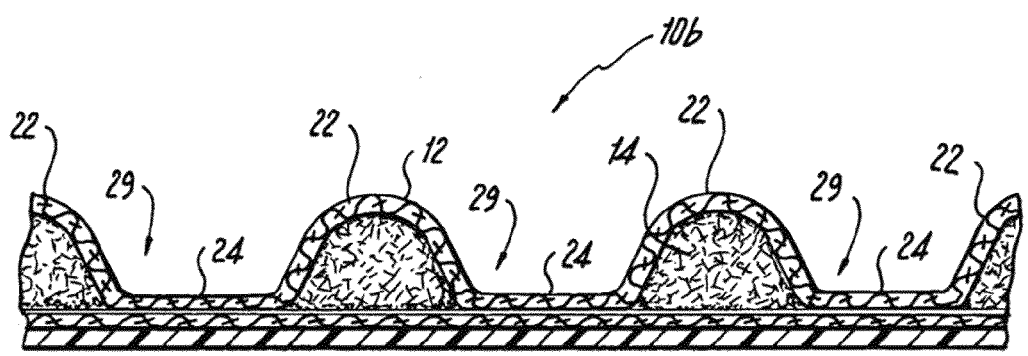
FIG. 10 is a sectional view taken of the absorbent article shown in FIG. 8 taken along line 10-10 in FIG. 8.

Reference is made to FIGS. 8-10 which depict a sanitary napkin 10b according to a third embodiment of the present invention. As shown in FIG. 9, the sanitary napkin 10b includes a includes a fluid permeable cover layer 12, an absorbent core 14, a transfer layer 16, and a fluid impermeable barrier layer 18. As shown in FIG. 9, the absorbent core 14 is arranged adjacent to the cover layer 12 and the transfer layer 16 is arranged between the absorbent core 14 and the barrier layer 18.

As best seen in the exploded view shown in FIG. 9, the absorbent core 14 includes a plurality of longitudinally extending material-free zones 20 that extend from an upper surface 19 of the absorbent core 14 to a lower surface 21 of the absorbent core 14. Each of the material-free zones 20 preferably has a width in the range of between 1 mm and about 10 mm and a length in the range of between about 50 mm and about 250 mm. Absorbent articles according to the third embodiment of the present invention preferably have between about 2 and about 7 longitudinally extending the material-free zones 20. Each of the material free zones 20 is spaced from an adjacent material-free zone 20 in the transverse direction by a distance from about 5 mm to about 30 mm. Each material-free zones 20 preferably extends over a surface area in the range of between about 50 mm$^2$ and about 4000 mm$^2$. In the particular embodiment of the invention shown in the FIGS. 8-10 the material-free zones 20 are linear in shape, parallel to each other, and equally spaced.

The absorbent core 14 further includes a plurality of longitudinally extending beams 25, each of the beams 25 being arranged in spaced relationship to an adjacent beam 25 and each of the beams 25 being separated from an adjacent beam 25 by one of the material-free zones 20.

As best seen in FIG. 10, the cover layer 12 includes a plurality of first regions 22 that are arranged in spaced relationship to the transfer layer 16 and a plurality of second regions 24 that are arranged in surface to surface contact with the transfer layer 16. The surface to surface contact of the cover layer 12 with transfer layer 16 in the second regions 24 essentially define a plurality of longitudinally extending gutters 29 in the body facing surface 11 of the napkin 10 that are coextensive with the path of the material-free zones 20. The absorbent core 14 preferably has a thickness of between about 0.5 mm and about 20 mm. The depth of each gutter 29 is in the range of between about 0.5 mm and about 20 mm.

Although not shown in the Figures, the sanitary napkin 10b may be provided with a secondary absorbent core arranged between the primary core 14 and the transfer layer 16, the secondary absorbent core including a plurality of material-free zones that correspond in shape and size to the material-free zones of the primary core 14.

Although not shown in the Figures, the areas of the napkin in which the gutters 29 are located may be colored a different color than the remainder of the absorbent article. For example, the areas in which the gutters 29 are located may be colored blue while the remainder of the napkin is generally white. By coloring the gutters 29 a different color than the remainder of the napkin, the enhanced wicking characteristics provided by the gutters 29 are visually communicated to a potential user of the absorbent article. The color may be imparted to the napkin by providing a color (e.g., ink) to the cover layer 12 and/or the transfer layer 16 and/or the barrier layer 18.

Cover Layer

The cover layer 12 may be a relatively low density, bulky, high-loft non-woven web material. The cover layer 12 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 12 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat.

No. 4,555,430 issued Nov. 26, 1985 to Chicopee. Using a fusible fabric increases the ease with which the cover layer may be mounted to the absorbent layers of the article and/or to the barrier layer.

The cover layer 12 preferably has a relatively high degree of wettability, although the individual fibers comprising the cover may not be particularly hydrophilic. The cover material should also contain a great number of relatively large pores. This is because the cover layer 12 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 12 should not lose their physical properties when they are wetted, in other words they should not collapse or lose their resiliency when subjected to water or body fluid. The cover layer 12 may be treated to allow fluid to pass through it readily. The cover layer 12 also functions to transfer the fluid quickly to the underlying layers of the napkin. Thus, the cover layer 12 is advantageously wettable, hydrophilic and porous. When composed of synthetic hydrophobic fibers such as polyester or bi-component fibers, the cover layer 12 may be treated with a surfactant to impart the desired degree of wettability.

Alternatively, the cover layer 12 can be made of a polymer film having large pores. Because of such high porosity, the film accomplishes the function of quickly transferring body fluid to the underlying absorbent layers. A suitable cover material of this type is commercially found on the STAYFREE Dry Max Ultrathin product distributed by McNeil-PPC, Inc.

The cover layer 12 may be attached to the underlying absorbent core 14, transfer layer 16, and/or the barrier layer 18, by adhesion and/or other suitable means know to those of skill in the art.

Absorbent Core

In one embodiment, the absorbent core 14 is a blend or mixture of cellulosic fibers and superabsorbent disposed therein. Cellulosic fibers that can be used in the absorbent core 14 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood pulps are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material.

The absorbent core 14 can contain any superabsorbent polymer (SAP) which are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc. In a specific example, the absorbent core is a material containing from 95% to about 40% percent cellulosic fiber by weight, and about 5% to about 60% SAP by weight.

In one specific embodiment of the invention, the absorbent core 14 is constructed from a mixture of fluff pulp, commercially available as RAYFLOC J-LD-E from Rayonier Products, Jessup, Ga., and superabsorbent polymer commercially available under the designation SA70N from Sumitomo Seika Chemicals Co., Ltd. Of Osaka, Japan, the mixture including 94% fluff pulp by weight and 6% superabsorbent polymer by weight.

Materials particularly suitable for use as the absorbent core preferably have a basis weight in the range from about 300 gsm (g/m$^2$) to 1000 gsm, a thickness in the range of about 0.5 mm to 20 mm, and a density in the range of about 0.015 g/cc to 2 g/cc.

Transfer Layer

Adjacent to the barrier layer 18 layer on its inner side is the transfer layer 16. As shown in FIGS. 3 and 4, the entirety of the transfer layer 16 is located adjacent the barrier layer 18. That is, the entire transfer layer 16 is located adjacent the barrier layer 18. The transfer provides the means of receiving body fluid from the cover layer 12 and holding it until the absorbent core 14 has an opportunity to absorb the fluid, and therefore serves as a fluid transfer or acquisition layer. In addition the transfer layer 16 functions to wick the fluid in the longitudinal and transverse directions of the napkin so that the full absorbent capacity of the napkin is utilized.

The transfer layer 16 is, preferably, has a larger proportion of smaller pores than the cover layer 12. These attributes allow the transfer layer 16 to contain body fluid and hold it away from the outer side of the cover layer 12, thereby preventing the fluid from re-wetting the cover layer 12 and its surface.

The transfer layer 16 may be composed of fibrous materials, such as wood pulp, polyester, rayon, flexible foam, or the like, or combinations thereof. Preferably, the transfer layer 16 is free of any superabsorbent polymer (SAP). The transfer layer 16 may also comprise thermoplastic fibers for the purpose of stabilizing the layer and maintaining its structural integrity. The transfer layer 16 may be treated with surfactant on one or both sides in order to increase its wettability, although generally the transfer layer 16 is relatively hydrophilic and may not require treatment. The transfer layer 16 is preferably bonded on both sides to the adjacent layers, i.e. the absorbent core 14 and the barrier layer 18.

Materials particularly suitable for use in the transfer layer 16 which the inventors have found contribute to reducing the penetration time have a density in the range of about 0.04 to 0.05 g/cc, a basis weight in the range from about 80 to 110 g/m$^2$ and a thickness in the range of about 1 to 3 mm. Examples of materials suitable for the first absorbent layer are through air bonded pulp sold by BUCKEYE of Memphis, Tenn. under the designation VIZORB 3008, which has a basis weight of 110 g/m$^2$ and VIZORB 3010, which has a basis weight of 90 g/m$^2$.

Barrier Layer

Underlying the transfer layer 16 is a barrier layer 18 comprising liquid-impervious film material so as to prevent liquid from egressing the sanitary napkin and staining the wearer's undergarment. The barrier layer 18 is preferably made of polymeric film, although it may be made of liquid impervious, air-permeable material such as repellent-treated nonwoven or micropore films or foams.

The barrier layer 18 may be breathable, i.e., permits vapor to transpire. Known materials for this purpose include nonwoven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 12 and the barrier layer 18 are preferably joined along their marginal portions so as to form an enclosure or flange seal that maintains the transfer layer 16 and absorbent core 14 captive. The joint may be made by means of adhesives, heat-bonding, ultrasonic bonding, radio frequency sealing, mechanical crimping, and the like and combinations thereof.

Figure 2:
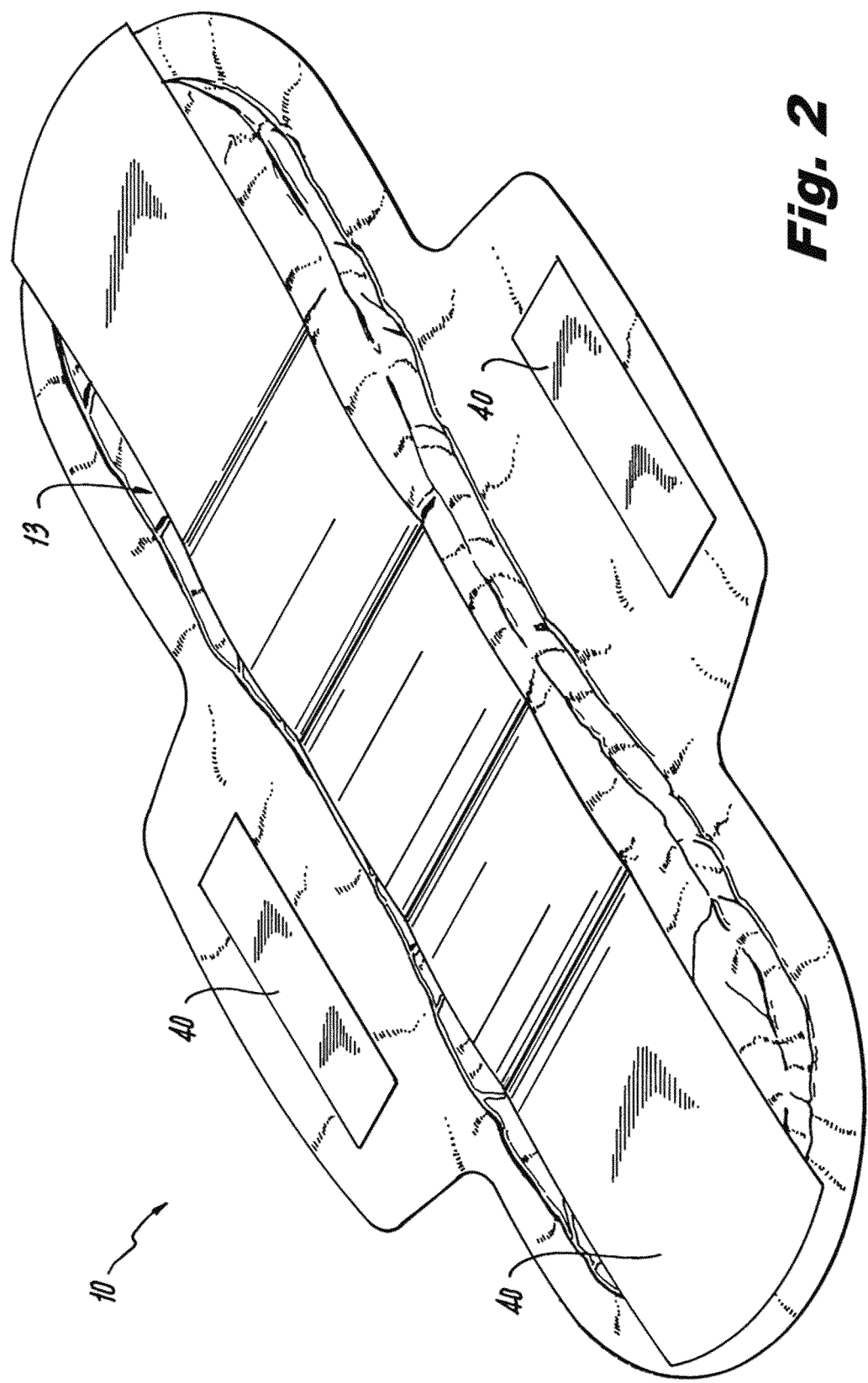
FIG. 2 is a bottom perspective view of the absorbent article shown in FIG. 1.

Positioning adhesive may be applied to a garment facing surface 13 of the barrier layer 18 for securing the napkin 10 to a garment during use. As seen in FIG. 2, the positioning adhesive may be covered with removable release paper 40 so that the positioning adhesive is covered by the removable release paper 40 prior to use.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

Test Procedures

Absorbent articles according to the present invention possess a combination of unique functional properties. The test procedures set forth below highlight each of these functional properties. Prior to conducting any of the described test procedures described below the test product should be conditioned for two hours at 21+/−1° C. and 50+/−2% humidity.

Procedure for Longitudinal Wicking Value (LWV) and Transverse Wicking Value (TWV)

Absorbent articles according to the present invention exhibit superior wicking in the longitudinal and transverse directions of the article. The Longitudinal Wicking Value (LWV) and Transverse Wicking Value (TWV) test set forth below illustrates the superior wicking characteristics of absorbent articles according to the present invention.

Absorbent articles according to the present invention have preferably have LWV greater than 60, more preferably greater than 70, and most preferably greater than 75. Absorbent articles according to the present invention preferably have a TWV greater than 35, more preferably greater than 40, and most preferably greater than 45.

The synthetic test fluid described below is used in the test method described below. The synthetic test fluid used in replacement of human menses due to its ease in preparation and accessibility of the ingredients.

The fluid is prepared by dissolving each of the following components into distilled water. Care should be taken to ensure that components are well dissolved. A rotating blade mixer or a magnetic stirrer should be used for mixing the components. In a large enough container, add the following components, making sure that the component is dissolved before adding the next one:

| Quantity/1 L | Reagent | Grade, purity | Supplier | Catalog No. |
|---|---|---|---|---|
| 9.0 g | sodium chloride | ACS reagent 99+% | Sigma-Aldrich | 223514 |
| 490.5 g | distilled water | N/AP | N/AP | N/AP |
| 10 g | 2-phenoxy-ethanol | puriss. 99.0% | Sigma-Aldrich (Fluka) | 77699 |
| 0.5 g | FD&C Red #40 | Food | A&C | C3465 |
| 490.5 g | Glycerol | ACS reagent 99.5% | Sigma-Aldrich | G7893 |

Figure 11:
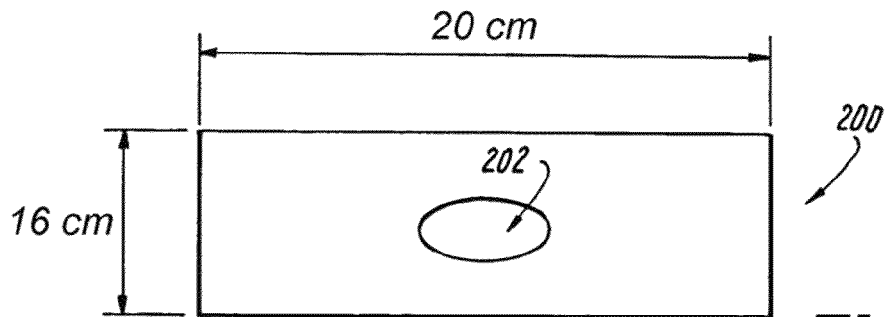
FIG. 11 is a top elevation view of a test plate used to measure the Longitudinal Wicking Value (LWV), Transverse Wicking Value (TWV), and Fluid Penetration Time (FPT) of an absorbent article.

The materials required to determine the LWV and TWV include the following:
- a poly(methylmetracrylate) (Plexiglas) template 200, shown in FIG. 11, having dimensions of 200 mm long× 60 mm wide×12.7 mm thick and an elliptical orifice 202 (30.8 mm×19 mm) in the center of the template;
- a calibrated electronic repeater pipette (HandyStep Electronic Repeating Pipet, Brandtech) with a 50 mL combi-syringe (or combi-tip) capable of delivering 5-10 mL at a rate of approximately 4 mL/s and fixed on a stand with the end of the tip placed vertically at 25.4 mm (1 inch) from the surface of the product;
- a calibrated stopwatch that has a precision of 0.01 s;
- a ruler graduated in millimeters (mm);
- a fine point permanent marker; and
- the test fluid prepared according to the procedure described above.

To obtain the LWV and TWV, the conditioned article is removed from its packaging, unfolded, placed on a flat surface (e.g. lab table). The Plexiglas plate 200 is placed and centered over the absorbent product, light hand applied pressure is applied to flatten the article, without compressing it, such that there is no substantial bending or folding of the article under the template 200.

Figure 12:
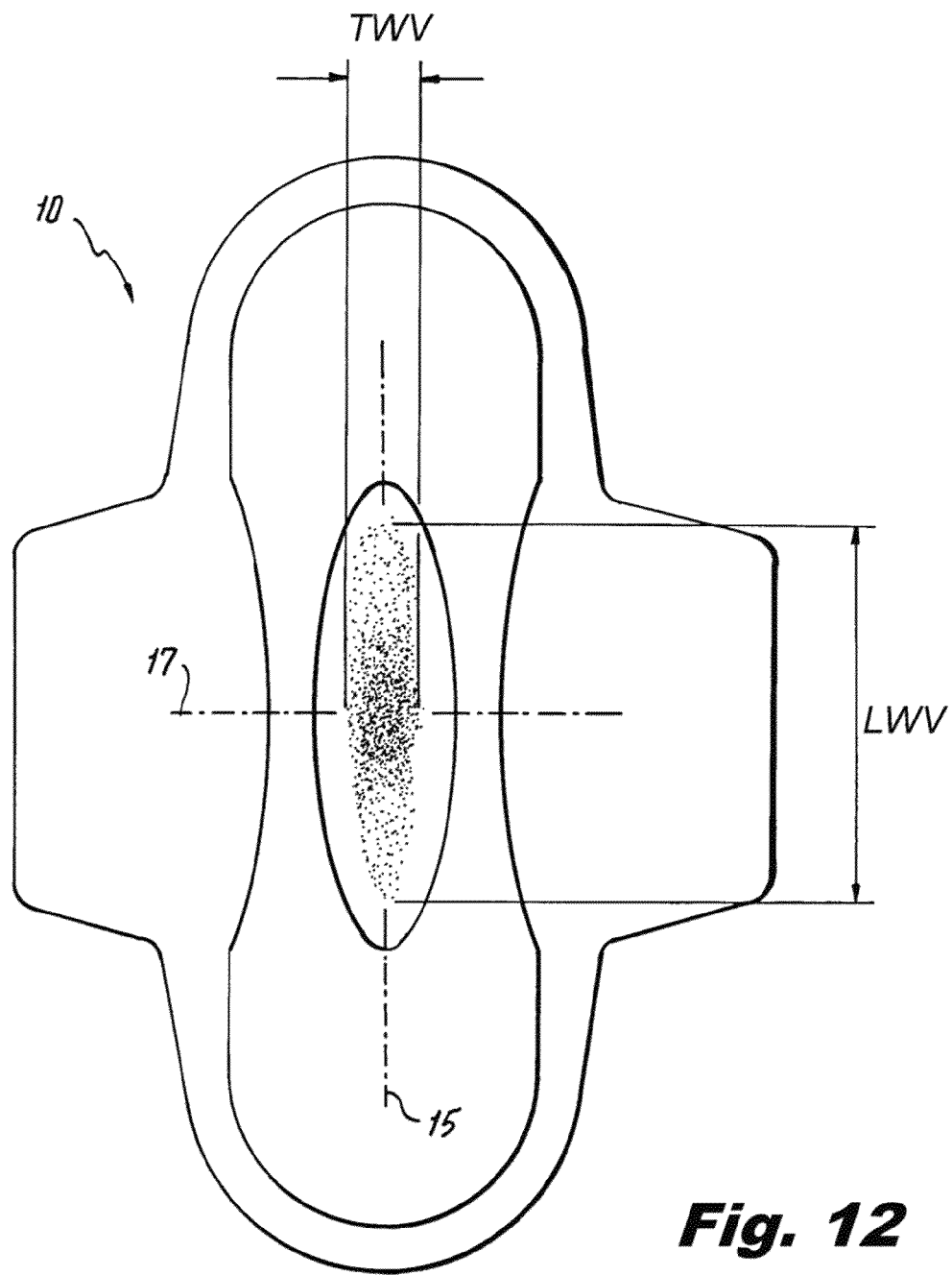
FIG. 12 is a schematic view depicting a stained absorbent article according to the present invention and the manner in which the Longitudinal Wicking Value (LWV) and Transverse Wicking Value (TWV) are measured.

A 50 mL combi-syringe (or combi-tip), placed on a repeater pipette, is filled with the test fluid, positioned vertically and fixed on a stand with the end of the tip placed approximately 1 inch from the surface of the product and above the center of the elliptical hole 202 of the plate. The article should be arranged such that the intersection of the longitudinally extending and transversely extending centerlines is positioned in the center of the hole 202. Then, 10 mL of test fluid is insulted to the article at a rate of approximately 4 mL/s. The stopwatch is started as soon as the repeating pipet button is pressed to dispense the volume. After 60 s, the plate is removed and the limits of the stain, along the longitudinally extending and transversely extending axes, are marked rapidly (within less than 10 s) with a marker. Only the continuous fluid stain limits found on the article cover are marked, fluid spots not continuous or linked to the rest of the fluid flow and/or observed in the lower layers of the absorbent product are not considered in the determination of the wicking distance. Using the furthest continuous points found along the longitudinally and transversely extending axes, a rectangle is drawn as shown in FIG. 12. The length of the rectangle measured in the longitudinal direction is the LWV and the length of the rectangle in the transverse direction is the TWV.

Thus the Longitudinal Wicking Value is the farthest continuous fluid displacement along the longitudinally extending centerline 15 of the article, and the Transverse Wicking Value is the farthest continuous fluid displacement along the transversely extending centerline 17. All distance values are measured with a ruler to a precision of 1 mm.

If the test fluid touches or runs over the edges of the plate 200 in the transverse direction within 60 s following the fluid injection, the sample is considered to have failed and a zero (0) TWV is attributed to that sample. If the absorbent article being tested is smaller than the test plate 200, then failure is defined as the moment when the fluid reaches the edges of the absorbent article in the transverse direction.

This procedure is repeated five times using three different samples of each type of absorbent article and an average LWV and TWV is calculated from these three repeats. If any of the five products fails, i.e. the fluid reaches the edges of the plate, then the reported average TWV is zero (0).

Procedure for Measuring Fluid Penetration Time (FPT)

Absorbent articles according to the present invention preferably have a fluid penetration time of less than 10 s, more preferably less than 8 s, and most preferably less than 5 s.

Fluid Penetration Time is measured by placing a sample to be tested under the template 200, shown in FIG. 11. The template 200 is arranged on the product sample so that the center of the elliptical orifice is aligned with the intersection of longitudinally extending centerline 15 and transversely extending centerline 17 of the product. The longitudinal axis of the elliptical orifice is aligned to the longitudinal axis of the product to be tested. Test fluid having the formula set forth above is utilized as the test fluid for the fluid penetration time procedure.

A graduated 10 ml syringe containing 7 ml of test fluid is held over the orifice plate such that the exit of the syringe is approximately 3 inches above the orifice. The syringe is held horizontally, parallel to the surface of the test plate. The fluid is then expelled from the syringe at a rate that allows the fluid to flow in a stream vertical to the test plate into the orifice and a stopwatch is started when the fluid first touches the sample to be tested. The stopwatch is stopped when a portion of the surface of the sample first becomes visible above the remaining fluid within the orifice. The elapsed time on the stopwatch is the Fluid Penetration Time. The average Fluid Penetration Time (FPT) is calculated from taking the average of three product samples.

Procedure for Measuring Rewet Potential

Absorbent articles according to the present invention preferably have a Rewet Potential of less than 1.0 g and more preferably less than 0.6 g.

The three product samples used for the Fluid Penetration Time (FPT) procedure described above are used for the Rewet Potential test described below.

The rewet potential is a measure of the ability of a napkin or other article to hold liquid within its structure when the napkin contains a relatively large quantity of liquid and is subjected to external mechanical pressure. The rewet potential is determined and defined by the following procedure.

The apparatus for the Rewet Potential test is the same as that set forth above with regard to the Fluid Penetration Time test and further includes a quantity of 3 inch×4 inch rectangles of Whatman #1 filter paper (Whatman Inc., Clifton, N.J.) and a weighing machine or balance capable of weighing to an accuracy of +/−0.001 g, a quantity of said Whatman paper, a standard weight of 2.22 kg (4.8 pounds) having dimensions 51 mm (2 inches) by 102 mm (4.0 inches) by approximately 54 mm (2.13 inches) which applies a pressure of 4.14 kPa (0.6 psi) over the 51 mm by 102 mm (2 inches by 4 inches) surface.

For purposes of the test procedure set forth herein, the same three product samples used for the fluid penetration test should be used for the rewet potential test. After the test fluid is applied within the orifice plate in the Fluid Penetration Time test described above, and as soon as the cover layer of the napkin first appears through the top surface of the fluid, the stopwatch is started and an interval of 5 minutes is measured.

After 5 minutes have elapsed, the orifice plate is removed and the napkin is positioned on a hard level surface with the cover layer facing upwards.

A fifteen (15) layer stack of the pre-weighed filter paper is placed on and centered over the wetted area and the standard 2.22 kg weight is placed on top of the filter paper. The filter paper and the weight are arranged over the absorbent article such that they are centered over the area to which the fluid was applied. The filter paper and the weight are arranged such that their longer dimensions are aligned with the longitudinal direction of the product. Immediately after placing the paper and weight on the product, the stopwatch is started and after a 3 minute interval has elapsed the standard weight and filter paper are quickly removed. The wet weight of the filter paper is measured and recorded to the nearest 0.001 grams. The rewet value is then calculated as the difference in grams between the weight of the wet 15 layers of filter paper and the dry 15 layers of filter paper.

The measurement should have at least three replicates and, if necessary, the weight is wiped clean before each run. The average rewet value (R) is then calculated from the three measured values.

EXAMPLES

Inventive Example

An inventive example of a sanitary napkin according to the present invention was constructed as follows.

The cover layer was a thermo bonded nonwoven cover having a basis weight of 16 gsm (polypropylene fibers) commercially available from Polystar under product code 142250. The core facing surface of the cover was treated with a construction adhesive commercially available from Bostik-Findley under product code H-2900. The adhesive was applied in an amount of 5.0 gsm over a 95 mm×230 mm portion of the cover. The treated side of the cover was placed on top of an absorbent core. The absorbent core was constructed with a material free zone of the type shown in FIG. 1 having a width of 30 mm as measured along the transversely extending centerline of the article and length of 100 mm as measured along the longitudinally extending centerline of the article. The material free zone extended over a surface area of 2305.91 mm$^2$. The core had a thickness of 5.5 mm. The gutter defined by the material free zone had a depth of 4.4 mm. The absorbent core was constructed from 5.0 g of wood pulp commercially available from Georgia Pacific under product code 111410 and 0.4 g super absorbent polymer commercially available from Sumitomo Seika Ltd. under product code SA70. The core had a density of 0.103 g/cc. The transfer layer was constructed from a 75 gsm airlaid commercially available from Buckeye of Memphis, Tenn. under product code X853-2. The transfer layer was placed on a polyethylene film barrier layer commercially available from Clopay under product code 113689. The transfer layer had a density of 0.058 g/cc. The transfer layer was attached to the core by applying adhesive, code H-2900 from Bostik-Findley, in an amount of 5.0 gsm over an area of 40 mm (width) by 100 mm (length). The transfer layer was attached to the barrier by applying adhesive, H-2900 from Bostik-Findley, in an amount of 3.6 gsm over the surface of the barrier layer.

Comparative Example #1

Comparative Example #1 was constructed from the same materials as described in the Inventive Example however the transfer layer was arranged between the cover layer and the core and the core was constructed as a solid layer, i.e. the core did not contain any material free zone.

Comparative Example #2

Comparative Example #2 was an Always Regular Maxi (lot #82434786421709 UPC3700030563).

Each of the Inventive Example, Comparative Example #1 and Comparative Example #2 were tested according to the test methods described above and the results thereof are summarized in Table 1 provided below.

TABLE 1

| (average of n = 3) | Inventive Example | Comparative Example #1 | Comparative Example #2 |
|---|---|---|---|
| Transverse Wicking Value (TWV) | 49.6 | 32.2 | 30.4 |
| Longitudinal Wicking Value (LWV) | 79 | 50.6 | 50.4 |
| Fluid Penetration Time (FPT) | 4.3 | 11.9 | 2.9 |
| Rewet Value | 0.49 | 0.05 | 2.7 |

As illustrated in the table provided above absorbent articles according to the present invention provide superior fluid handling characteristics when compared to comparable prior art articles.

We claim:
1. An absorbent article comprising:
a longitudinally extending centerline;
a transversely extending centerline;
a liquid permeable cover layer having a body facing surface;
a liquid impermeable barrier layer;
an absorbent core arranged adjacent to the cover layer;
a transfer layer arranged between the core and the barrier layer, wherein an entirety of said transfer layer is arranged adjacent to the barrier layer;
wherein the absorbent core includes an upper surface and a lower surface and a material-free zone extending from the upper surface to the lower surface wherein the material-free zone is:
  a. substantially elliptical in shape;
  b. extends over an area between about 400 mm$^2$ and about 6000 mm$^2$; and
  c. centrally aligned with respect to the longitudinally extending centerline and the transversely extending centerline, having:
    i. a length as measured along the longitudinally extending centerline in the range of about 40 mm to about 250 mm; and
    ii. a width as measured along the transversely extending centerline of about 10 mm to about 60 mm;
wherein the cover layer includes a first region arranged in spaced relationship to the transfer layer and a second region arranged in surface to surface contact with the transfer layer such that the transfer layer, absorbent core and the cover layer cooperate to define a longitudinally extending gutter in the body facing surface of the article, the gutter having a depth in the range of between about 0.5 mm and about 20 mm.

* * * * *